United States Patent [19]

Vaillancourt

[11] Patent Number: 4,966,586

[45] Date of Patent: Oct. 30, 1990

[54] CLOSED SYSTEM OVER-THE-NEEDLE I.V. CATHETER

[76] Inventor: Vincent L. Vaillancourt, 14 Bunyan Dr., Livingston, N.J. 07039

[21] Appl. No.: 453,043

[22] Filed: Dec. 12, 1989

Related U.S. Application Data

[63] Continuation of Ser. No. 93,420, Sep. 4, 1987, abandoned.

[51] Int. Cl.[5] ............................................. A61M 5/178
[52] U.S. Cl. .................................... 604/164; 604/167; 604/122
[58] Field of Search ....................... 604/164, 166–169, 604/129, 190, 122, 125, 297, 201, 165

[56] References Cited

U.S. PATENT DOCUMENTS

| | | | |
|---|---|---|---|
| 3,401,692 | 9/1968 | Harris, Jr. ........................... | 604/125 |
| 3,743,095 | 5/1973 | Santomieri ........................... | 604/168 |
| 3,776,239 | 12/1973 | Cooley ............................... | 604/122 |
| 3,977,400 | 8/1976 | Moorehead .......................... | 604/168 |
| 4,066,556 | 1/1978 | Vaillancourt ........................ | 604/190 |
| 4,193,400 | 3/1980 | Loveless et al. ..................... | 604/168 |
| 4,269,186 | 5/1981 | Loveless et al. ..................... | 604/168 |
| 4,314,555 | 2/1982 | Sagae ................................. | 604/168 |
| 4,468,224 | 8/1984 | Enzmann et al. .................... | 604/164 |
| 4,496,348 | 1/1985 | Genese et al. ....................... | 604/167 |
| 4,505,440 | 4/1986 | Tchervenkov et al. .............. | 604/167 |
| 4,525,157 | 6/1985 | Vaillancourt ........................ | 604/168 |
| 4,652,256 | 3/1987 | Vaillancourt ........................ | 604/164 |
| 4,755,173 | 7/1987 | Konopka et al. .................... | 604/167 |
| 4,869,718 | 9/1989 | Brader ................................ | 604/164 |

Primary Examiner—C. Fred Rosenbaum
Assistant Examiner—Kathleen A. Daley
Attorney, Agent, or Firm—Kenyon & Kenyon

[57] ABSTRACT

An over-the-needle I.V. catheter is depicted for attachment to an I.V. fluid supply. This product is primed prior to puncture of a patient's blood vessel. This product includes a catheter hub with an attached flexible catheter having its forward end tapered to provide penetration capability. This hub has a connection to I.V. fluid supply. The catheter is sized to accept a needle which in mounted condition has its sharpened tip extending from the entering end of the catheter. Venting is provided. The needle when and as withdrawn leaves a hole in a seal which in this product utilizes a resilient disc which may or may not be slit. Two washers are employed to assist in sealing of this needle withdrawal hole. A threaded cap is rotated just prior to use to bring this resilient disc under compression. Alternate means is provided by a bayonet-type of force actuation and lock.

19 Claims, 3 Drawing Sheets

Fig. 1A

PRIOR ART

CLOSED SYSTEM OVER-THE-NEEDLE I.V. CATHETER

This application is a continuation, of application Ser. No. 07/093,420, filed Sept. 4, 1987 now abandoned.

BACKGROUND OF THE INVENTION

1. Field of the Invention

This invention relates to an over-the-needle I.V. catheter. More particularly, this invention relates to a closed system over-the-needle intravenous catheter.

2. Description of the Prior Art

The problem of providing an infusion device for a patient has been addressed in several patents, among which are U.S. Pat. Nos. 3,851,647; 4,073,297; 4,311,137; 3,313,299; 4,037,595; 4,016,879; 3,875,938; 4,496,348; 4,531,937 and 4,529,399.

It is to be noted that the U.S. Pat. No. 4,311,137, identified above, although providing a needle, flashback indicator, side arm and catheter and providing wings for securement, initially has the catheter 18 extending beyond the needle tip of the needle 76. This catheter end beyond the piercing end of the needle during sterilization, storage and shipment usually bends sufficiently so that the catheter is cut when the needle is pushed forwardly for penetration of the skin of the patient. This is highly undesirable. As described, the air is vented beside the seal-off plug and fluid comes out by the needle holder. This is not a "closed system" in that fluid as it is fed into the hub to purge air has the fluid and air open to the atmosphere as and when the device is unwrapped for use. The teaching of this patent is that the needle is advanced by the attendant to extend beyond the catheter tip. When and as the needle is advanced within the catheter and without assembly apparatus as provided by an assembly machine, the alignment of the catheter and needle must be very precise. Otherwise, the sharpened end of the needle cuts the flexible plastic catheter. The practitioner has no such assembly alignment apparatus. The seal assembly is initially vented to atmosphere, then the needle holder is moved forward to exert a side compressive force provided by the formed taper.

U.S. Pat. No. 3,851,647, although having a catheter over a needle, anticipates sealing of the needle hole with a resilient flap. U.S. Pat. No. 4,073,297 also provides a rubber plug as a seal of the withdrawn needle. The opposed openings 20 in the catheter are not very tiny so as to exclude an inflow of blood to and into the interior of the catheter. The plug 38 is removable, but clamping of portion 36 is effected to exclude fluid and blood flow. U.S. Pat. No. 3,313,299 relies on resilient plug 30 for a seal after the trocar 48 is withdrawn. In U.S. Pat. No. 4,531,937, the expelling of air is through plug 30 and there is no assurance of purging of the air unless the catheter 18 has an open entering end, which is not desired. U.S. Pat. No. 4,496,348 utilizes a spring to exert a force on the rubber seal after needle withdrawal. In sterilization and storage, this spring exerts a force on the rubber plug 30 and causes a small binding to develop which results in adherence of this rubber to the needle and requires excessive force for removal of the needle from this plug. For this reason, the product is currently not available nor has the problem of air purging been addressed.

Also of note are U.S. patents directed to the use of resilient sealing of a needle shank and providing a desired seal of the passage of the withdrawn needle shank. Among these patents are: U.S. Pat. Nos. 4,610,674; 4,610,665; 4,177,814; 4,626,245 and 4,430,081. These proposed sealing procedures anticipate prior seal sterilization and storage. Positioning of the trocar through the seal is just prior to or during use.

In the patents noted above and showing a catheter over the needle and as connected to an administration set and prior to puncture of a blood vessel, a deficiency exists as there is no complete removal procedure for insuring that air present is completely purged from the system.

In known systems, intravenous fluid administration devices often include a holder carrying a plastic catheter and a removable needle cannula extending through the catheter and past the distal tip of the catheter for inserting the needle and catheter through the skin and into a body vessel, such as a vein of a patient. If the venipuncture is successfully performed, the needle is removed and a source of infusion liquid, such as glucose, blood, saline solution or other liquid, is connected to the holder to supply the infusion liquid to the vein.

Air must, of course, be removed from the catheter placement device, and the infusion liquid source connected to it without introducing air into the device in order to avoid any air being introduced into the vein of the patient. Generally, after the venipuncture and removal of the needle, blood is allowed to flush the air from the catheter holder, and a liquid-filled delivery tube from the infusion liquid source is then carefully connected to the blood-filled device.

Performing the above steps without introducing air into the system is relatively tedious, and generally results in blood escaping from the device and soiling clothing or the like or requiring the use of absorbent materials to catch the escaping blood. Also, the above connection of the infusion liquid source to the device requires manipulation of parts while the catheter is in the vein of the patient, and this tends to increase patient discomfort and the danger of damage to the patient. This procedure is shown in FIG. 1 and identified as Prior Art.

The most popular I.V. Catheter used today is known as an over-the-needle catheter. In excess of seventy percent of all I.V. catheters are placed using this technique. The major advantages claimed for this produce are: its ease of insertion and the ability to be placed in peripheral veins. The major disadvantage is having to connect a pre-primed I.V. administration set to the catheter hub. This requires manipulation and/or dexterity. Numerous journal articles have addressed the question of contamination resulting from this procedure. It is generally believed that a significant percentage of the incidences of sepsis is directly attributed to this manipulation. With the advent of AIDS and its potential for communicating the disease by way of the bloodstream, the need for performing "bloodless" venipuncture has become more acute.

The above-noted prior art is deficient in a number of areas. It does not provide for a simple, effective means for removing all air from the systems prior to insertion of the catheter into a patient. This is essential to provide a safe product. Means is not provided for minimizing drag of the needle during removal whereat and whereby the practitioner is able to readily remove the needle from the catheter without disturbing the positioning of the catheter in a blood vessel (usually a vein) and concurrently seal off the passage. The above and known patents and devices do not provide an effective and positive seal of the passageway during removal of the needle. U.S. Pat. No. 4,496,348 is only directed to a seal of the hole left by the withdrawal of the needle, but this constant spring force causes a welding or excessive friction to be developed which disturbs a smooth insertion procedure and use.

In the summary immediately below, in the description and in the claims, that member to which the catheter is attached is identified as "hub" and that member to which the needle is secured is identified as "holder."

SUMMARY OF THE INVENTION

Accordingly, it is an object of the present invention to provide an improved fluid administration device wherein the above disadvantages are substantially obviated and to provide an improved method of connecting a source of infusion fluid to the vascular system of a patient.

This invention is also directed toward a means for eliminating a "wet" hookup of a catheter hub to an I.V. administration set. This invention also eliminates practitioner dexterity as criteria for preventing blood egress into the surrounding environment. Further, in one embodiment it is directed at providing a closed system that is not vulnerable to bacteria invasion within the fluid path of the system during and after the catheter insertion procedure. If so desired, I.V. administration sets may be changed after catheter placement without concern for bacteria invasion at the vessel site by way of the catheter fluid path.

The invention consists of having an extension set which contains a bacteria-retentive filter external but pre-connected to the over-the-needle I.V. catheter. Air-eliminating means is provided to allow the catheter with filter extension set to be pre-primed to eliminate all air in the system prior to making the blood vessel puncture. After the puncture is made, means are provided for removing the needle-holder assembly without blood leakage such that the entire assembly is now closed. In this way, a "bloodless" puncture may be readily performed.

In one embodiment, the over-the-needle catheter is comprised of a hub from which a hollow catheter extends and in which a sealing disc is mounted. In addition, a hollow needle extends through the catheter and through the disc in sealed relation while a needle holder is connected to the needle and extends from the hub. The needle holder has also a flash-back chamber in communication with the hollow needle for receiving an indication of blood therein upon penetration into a blood vessel. In accordance with the invention, a means is provided for selectively compressing the sealing disc through which the hollow needle passes to impose a compressive force on the disc after withdrawal of the needle from the disc in order to close any opening therein.

In another embodiment, an I.V. administration set is hooked up directly to the I.V. catheter side arm outlet. Prior to vessel puncture, the I.V. catheter is primed by allowing fluid to first enter the administration set, then enter the catheter and hub assembly. When the catheter space is filled, the I.V. administration set is clamped off and the vessel puncture procedure performed. After flash-back is observed in the needle holder, the needle is withdrawn. The opening created by the needle closes immediately due to prior manipulation and resulting compression of a resilient disc which provides an automatic sealing means. The catheter is provided with a tapered forward end and this tapered end is made as a snug fit on the shank of the needle. A small air passage means, such as a very tiny slit, pinhole or a small air passageway formed in the catheter tip or near this snug-fit tapered end and under pressure is sufficient to pass fluid therethrough. Air venting means, if not a slit or pinhole, may be provided at this tip end by a small groove or the like in the exterior surface of the needle or forming the contoured forward portion of the catheter with a bore which locally is not completely tight to the needle, i.e., this internal bore may be a slight eccentric.

As indicated, the air venting means may be achieved by slitting the catheter just in back of the tapered seal-off area between the catheter and needle shank with a small incision. This incision may be 1/32" long by 0.001"-0.002" wide and accomplished using a very thin razor blade. Air passage means may also be made by a small puncture as effected by using a sharpened end of a needle. Also, means creating a small passageway between the catheter tip and needle provides this air passageway. A scoring needle may be used in the bore of the catheter or the penetrating needle may have a small dimple or localized groove.

In one embodiment, the I.V. delivery line has a bacteria filter mounted in the flow path, said filter having a pore size of 0.2 microns or smaller, to prevent bacteria ingress in the line to the catheter holder.

There are illustrated two resilient discs used in the needle puncture-valve closing. In one embodiment, the disc is punctured by the insertion therethrough of the needle, and in the other embodiment the disc is provided with a slit so as to reduce the effort of insertion and/or withdrawal. In both instances, the disc is compressed just before the over-the-needle I.V. catheter is inserted into the patient. The compressive force is manipulative by the practitioner just prior to use. A threaded cap is rotated to provide this force. In an alternate embodiment, a cap having at least one bayonet-type groove is slideable on the rear portion of the catheter hub and a pin portion of this hub is adapted to be engaged by said groove. The forward movement of this cap compresses a spring or resilient member to provide a determined compression.

The embodiments to be illustrated and described provide several novel advantages over prior known devices. First, this is a "closed" system for an over-the-needle I.V. catheter. Second, the tip end of the catheter is provided with a very small air escape means that also indicates under a small head of fluid pressure the assurance that air purging has been achieved. Third, there is a bacteria filter in the inflow line to the hub to insure that the fluid supply is bacteria-free. Fourth, a sealing means allows the needle to be withdrawn with a desired minimum of effort while sealing the hole area against leakage.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there has been chosen a specific embodiment of the "closed system" over-the-needle I.V. catheter for use with administration of fluids to a patient as adopted for use in penetration of the patient's skin and showing a preferred means for insuring purging of air from said catheter system. This specific embodiment has been chosen for the purposes of illustration and description as shown in the accompanying drawings wherein:

BRIEF DESCRIPTION OF THE DRAWINGS

FIG. 1 represents diagrammatic views of the "prior art" procedure for inserting a catheter in the patient's blood vessel, FIG. 1 A showing a typical I.V. fluid delivery system as provided in a hospital, FIG. 1 B diagrammatically showing a conventional needle and catheter assembly, FIG. 1 C showing a puncture of the patient's skin and penetration to and into the blood vessel, FIG. 1 D showing the conventional procedure for withdrawing a needle from the punctured vessel and the now placed catheter, FIG. 1 E illustrates the positioned catheter and retention of blood flow while an I.V. connector end is being brought to the catheter hub, and FIG. 1 F represents the positioned catheter and I.V. connector in assembled flow condition;

FIG. 2 represents a side view of a catheter apparatus of this invention and having a "closed system" over-the-needle I.V. catheter in an assembled condition, ready for hookup to a fluid delivery I.V. tubing and insertion into the skin of a patient;

FIG. 3 represents an expanded isometric view of a rubber slit valve used with the needle of this invention;

FIG. 4 represents a sectional view of the catheter in an assembled condition utilizing the elements of FIGS. 2 and 3;

FIG. 5 represents a side view of the catheter of FIG. 4 assembled to an I.V. bottle of an administration set;

FIGS. 6 A and 6 B represent side views of the catheter of FIG. 5 with a filter interposed in and connected to the conductor providing fluid flow, FIG. 6 A representing the placement of the assembly in inserted condition and FIG. 6 B representing this same apparatus with the needle moved to the withdrawal condition;

FIG. 7 represents an expanded isometric view of a rubber disc and washers providing an alternate seal closure;

FIGS. 8 A and 8 B represent fragmentary side and end views of an alternate means for providing an air vent, with FIG. 8 A showing an enlarged sectional view of a small dislocation of the needle configuration, and FIG. 8 B showing this dislocation in the needle, this view taken on the line 8 B–8 B of FIG. 8 A and looking in the direction of the arrows, and FIGS. 9 A, 9 B, 9 C and 9 D represent fragmentary views showing an alternate means of selectively exerting a compressive force on a resilient sealing disc, FIG. 9 A a sectional, partly fragmentary diagrammatic view illustrating the alternate compressive force means and utilizing a bayonet-lock arrangement with the spring in a mounted, apparatus-stored condition, FIG. 9 B fragmentarily showing the view of 9 A but with the spring in a compressed condition and with the device ready for use, FIG. 9 C showing an outside view of the rear of the catheter hub and, in particular, the bayonet-type groove and pin by which the compressive force is applied, and FIG. 9 D is an isometric view of a resilient tubular member that may be utilized rather than a spring as shown in FIG. 9 A.

In the following description and in the claims, various details are identified by specific names for convenience. These names are intended to be generic in their application. Corresponding reference characters refer to like members throughout the several figures of the drawings.

Figures 1A, 1B, 1D, 1E, 1F:
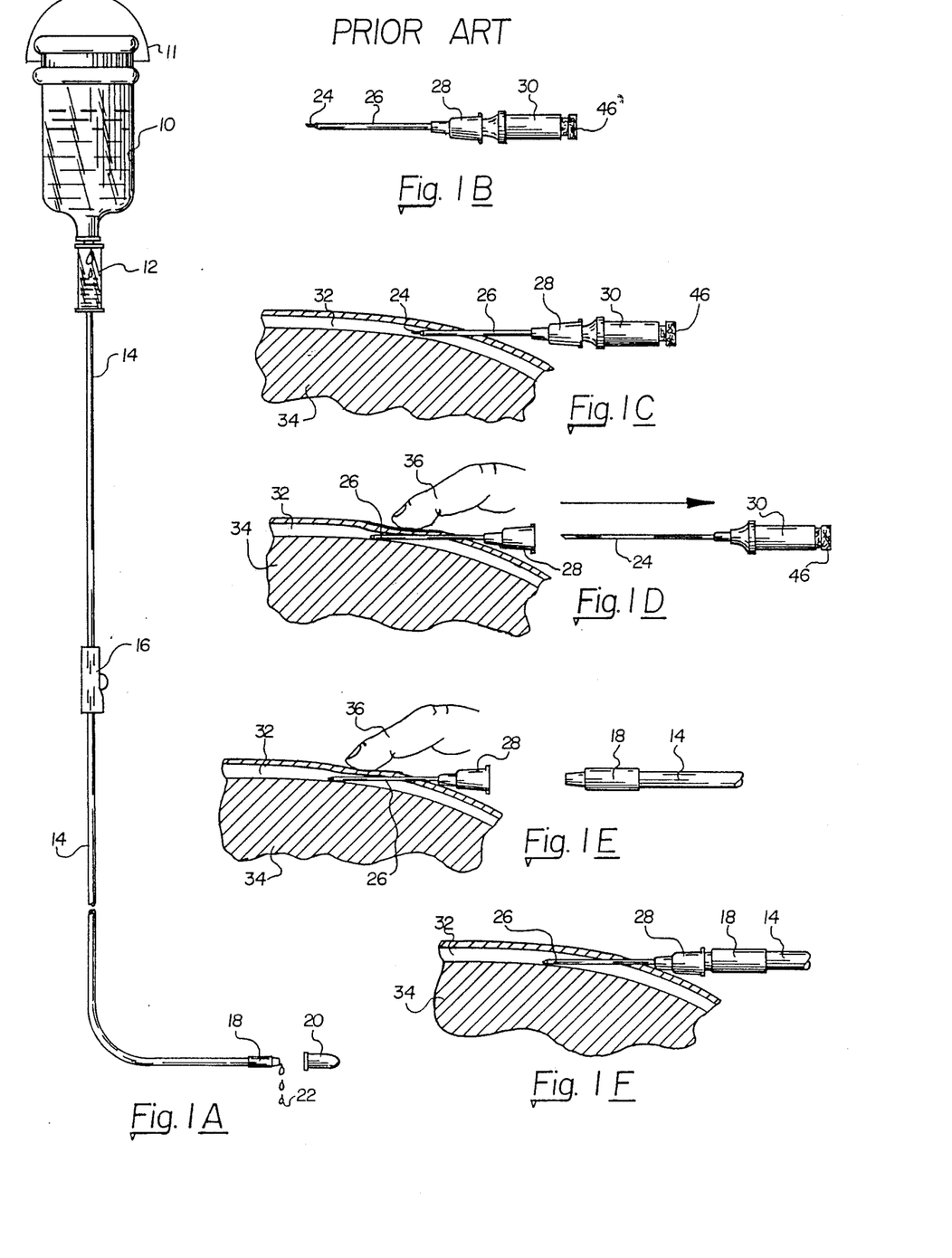

DESCRIPTION OF THE EMBODIMENT OF FIGS. 1 A THROUGH 1 F

Referring next to the drawings and in particular to FIGS. 1 A through 1 F, there is depicted the conventional "prior art" procedure as utilized in and by hospital attendants, nurses, doctors, and the like. In FIG. 1 A is diagrammatically shown a fluid storage and delivery bottle 10 conventionally suspended by and with a bail device 11. An administration set including a drip chamber 12 is hooked up to the stopper of this bottle. I.V. tubing 14 includes a roll clamp 16 interposed thereon. This I.V. tubing 14 continues to a discharge connector 18 usually closed against contamination by a cap 20. The cap 20 is removed for fluid 22 to proceed through the tubing 14 until the air in the line is purged therefrom. The clamp 16 is manipulated for this purpose.

In FIG. 1 B a standard needle 24 passes through the bore of a catheter 26 and a hub 28 to which the catheter is attached. A needle holder with a flash-back indicator 30 is connected to this needle and provides means to ascertain when the needle enters a blood vessel of the patient.

In FIG. 1 C is diagrammatically shown the assembled device of FIG. 1 B in placed and penetrated condition. The needle 24 and catheter 26 have penetrated the patient's skin to the extent that the sharpened end of the needle has entered a vessel 32 of the body 34 of the patient. This desired penetration is indicated with a flow of blood to and into the needle holder with a flash-back indicator 30.

In FIG. 1 D the needle 24 and the connected needle holder with flash-back indicator 30 have been separated and withdrawn from the catheter 26 and its hub 28, and to prevent unwanted escape of blood from the placed catheter 26, the attendant uses his or her finger 36 to press the blood vessel 32 into a more-or-less closed condition so as to reduce or stop the escape of blood from the patient through the catheter lumen.

In FIG. 1 E the finger 36 continues to press the vessel 32 around and to the catheter 26 and with another hand the attendant brings the now uncovered connector 18 toward and to hub 28.

In FIG. 1 F the completed hookup is depicted with the fluid in the I.V. bottle 10 delivered through tubing 14 and connector 18 to and through hub 28 into catheter 26 in vessel 32. It is assumed that connector 18 is seated in hub 28 so as to have no leaks.

Figures 2, 3, 4, 9A, 9B, 9C, 9D:
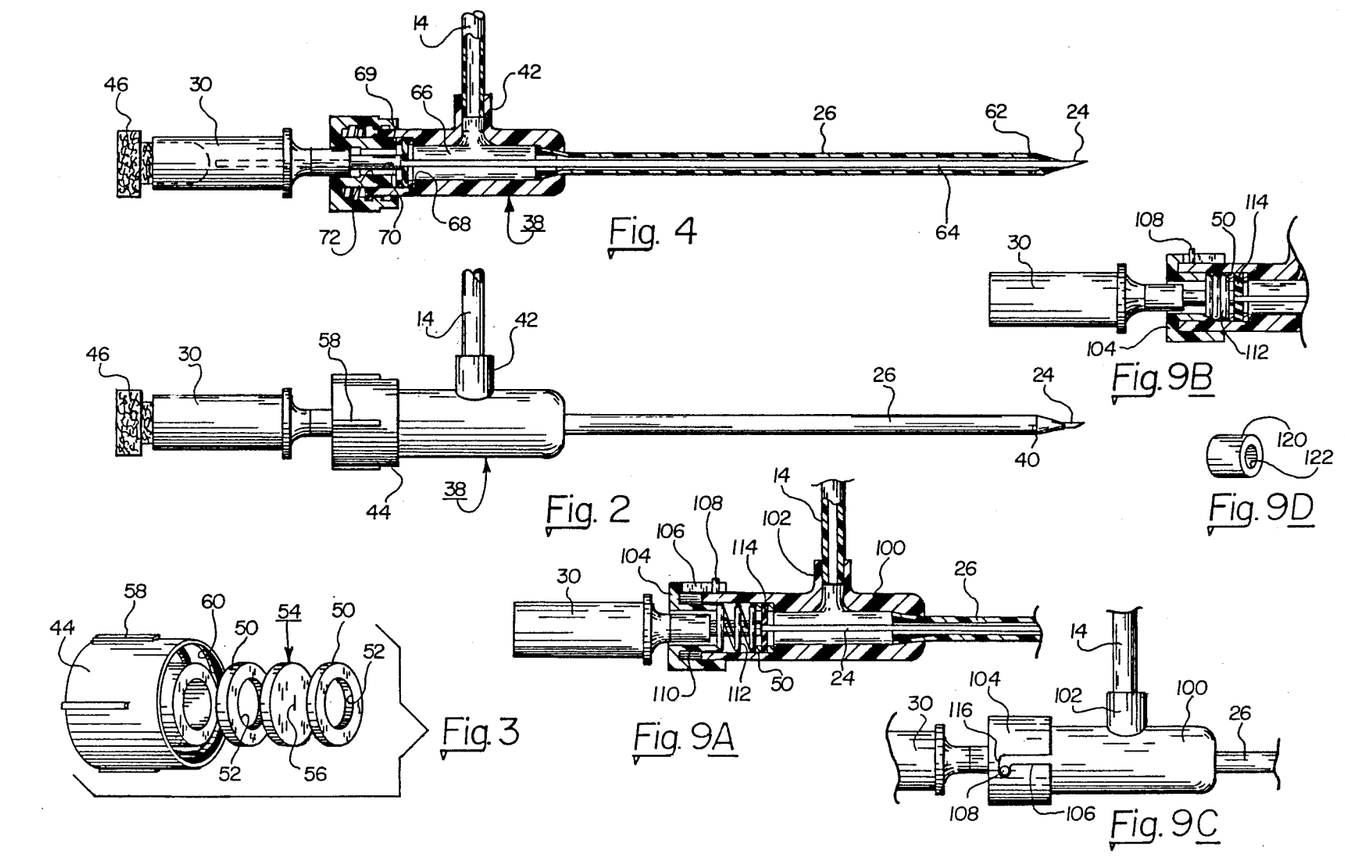

EMBODIMENT OF FIG. 2

In FIG. 2 is shown the exterior appearance of one embodiment of this invention. Needle 24, catheter 26 and needle holder with flash-back indicator 30 are very much like those discussed in the prior art showing. In FIG. 2, a flexible catheter 26 is secured to a catheter hub generally indicated as 38. The catheter includes a slit 40, which slit is constructed or provided so as to discharge a small drop of fluid under a small amount of pressure. Although described as a slit, this fluid flow passage 40 is made very tiny and may be made with a sharpened needle end. This discharge passageway is only sufficient to allow fluid to be expelled as drops when pressure is provided in the connected administration set. This disposed fluid flow provides an indicator that any and all air in the connected system has been purged. This discharge passageway allows fluid to be expelled but during normal operation does not allow blood to pass.

This hub 38 includes a side arm 42 which has a socket for receiving and retaining the connected end of I.V. conducting tubing 14. It is to be noted that the connector 18 of FIG. 1 A is not present but may be utilized, and no patentable distinction is ascribed thereto. The rear of hub 38 is formed with male threads adapted to receive a threaded cap 44 which retains rubber slit valve elements that are discussed here below in connection with FIG. 3. The flash-back indicator chamber 30, which is connected to and is in flow connection with the needle 24, is a clear to translucent tubular member which has an air vent closure member 46. This closure member 46 permits air in the needle holder to be expelled by the inrush of blood into the chamber 30, but does not readily permit passage of blood. This closure member 46 is made of a porous plastic material that is conducive to the passage of air, and not fluid, and is conventionally a press fit in the bore of the needle holder tubular chamber providing the flash-back capability. The slit 40 as noted above is preferably about one thirty-second of an inch in length and preferably is longitudinally arrayed. A very sharp knife or razor blade is employed so that the slit is a maximum of about one- to two-thousandths of an inch in width.

EMBODIMENT OF FIG. 3

In FIG. 3 is shown a slit valve depicted as used with this catheter device and employing a resilient rubber disc 54 having a slit 55 and a thickness less than a cross sectional dimension, i.e. diameter, thereof. The needle 24 (FIG. 2), when and as inserted through the slit 55 of the disc 54, causes the resilient member over a period of time to take a permanent "set" which promotes blood leakage when and as the needle is withdrawn from the catheter. This permanent "set" is accelerated by the process of sterilization. Shelf storage life promotes this unwanted leakage. As shown in FIG. 3 this valve means includes means for selectively compressing the disk 54 in order to impose a compressive force on the disk 54 after withdrawal of the needle 24 in order to close any opening therein. As illustrated, this means includes a plastic washer 50 having an aperture 52 therethrough. As shown there are two like washers 50, one of each arrayed on each side of the disc 54.

A threaded tubular cap generally identified as 44, has ribs 58 formed thereon with these ribs assisting in the manipulative rotation of this cap. This cap is formed with internal threads 60 providing means for in-and-out movement of the cap toward and away from hub 38. This valve and the sealing provided therewith is in conjunction with the hub construction and assembly of FIG. 4. This cap 44 is rotated from a released position to a clamping position relative to the hub 38 in order to impose a compressive force on the disk 54 via the rings 50 just prior to insertion and use of the over-the-needle catheter and needle into the blood vessel of the patient.

EMBODIMENT OF FIG. 4

In FIG. 4 are shown, in section and partly in a side view, the several components of this "closed system" over-the-needle I.V. catheter of this invention. In this FIG. 4, the catheter 26 is shown with a conventionally formed tapered front end 62 configured to tightly engage and slide on the shank of needle 24. This end 62, although tight to the needle shank to the rear, leaves a space providing a slight passage 64 which is sufficient for the flow of fluid alongside the needle 24. The catheter hub 38 is made of molded plastic and retains said catheter 26 so that this passage 64 is open to an interior cavity 66 which is in flow communication with the side arm 42. This cavity 66 extends to a shoulder 68, which is the interior end of a slightly larger diameter for the washers 50 and disc 54. In assembled condition, the forward end 70 of the needle holder enters the interior diameter 72 of molded hub 38 and rests against the rearmost washer 50. The flash-back indicator 30 of the needle holder and the porous air vent plug 46 are shown in the mounted condition.

In the sectional view of FIG. 4, the sealing components of FIG. 3 are shown in mounted condition, with washer 50 (inner) abutting shoulder 68, then disc 54 is disposed, and then another (outer) washer 50. The molded hub 38 is formed with exterior threads 69 which are sized and compatible with the female threads 60 provided in cap 44. The reduced diameter 72 of the needle holder 30 may pass through the aperture 52 in the rearmost washer 50 and engages disc 54 which provides the limiting stop. The washers 50 may have the apertures 52 of sufficient size for the reduced diameter 72 to pass therethrough and engage disc 54 or the aperture 52 may be only sufficient size for the free passage therethrough of the needle 24 whereat the portion 72 engages the face of the outer washer 52.

Figures 5, 6A, 6B, 7, 8A, 8B:
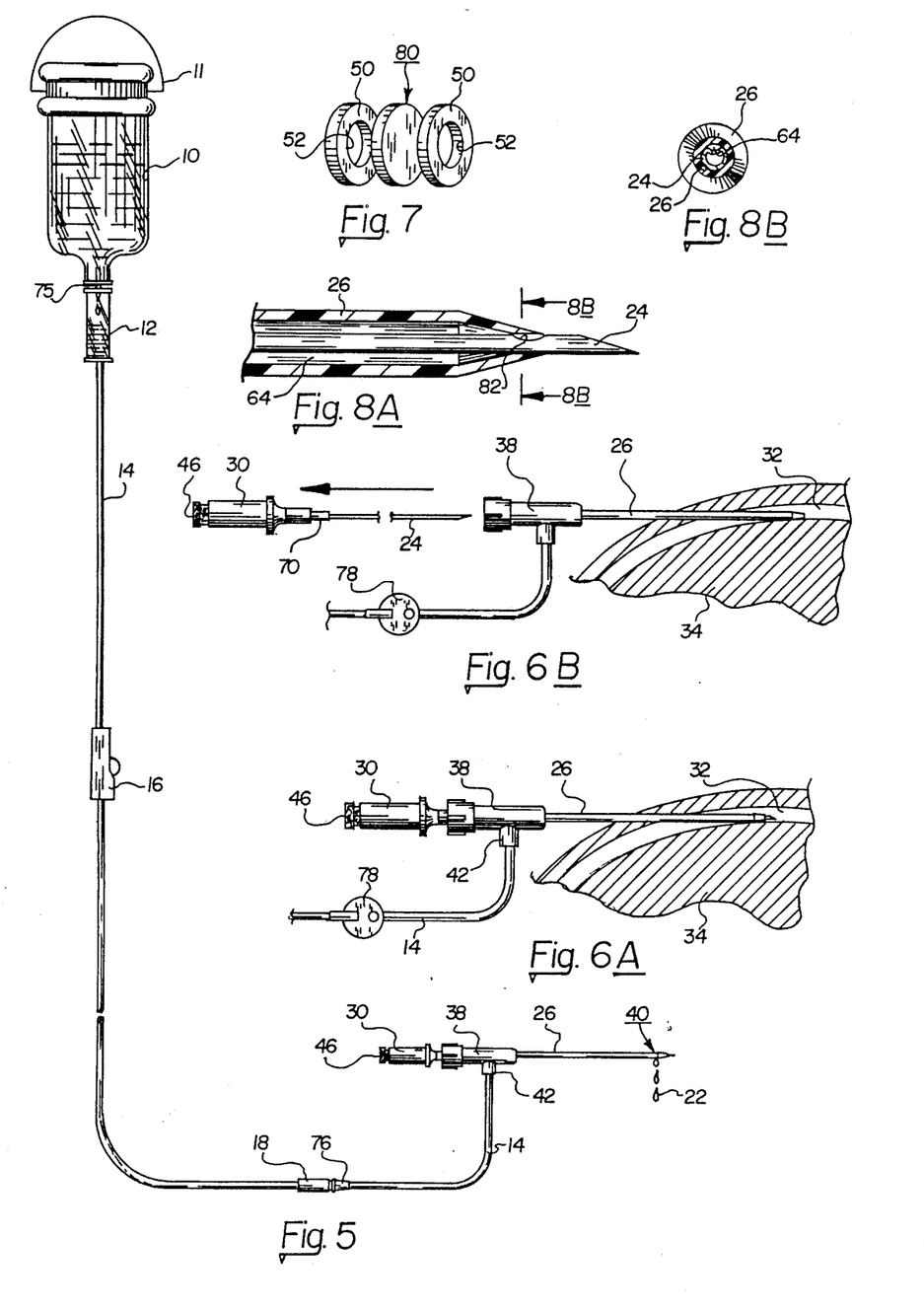

EMBODIMENT OF FIG. 5

In FIG. 5, the bottle 10, use hanger device 11, drip chamber 12, roller clamp 16 and I.V. tubing conductor 14 are shown connected to the side arm 42 of the catheter hub 38. A spike 75 is shown in this FIG. and is conventional in administration sets. An air vent (not shown) is provided with the spike to allow atmospheric air to enter the bottle so as to prevent a development of vacuum. It is to be noted that the pressure provided by the bottle 10 above the catherter device is sufficient for the flowing of fluid from the bottle 10 through the I.V. tubing to and through the slit or puncture 40 so that the delivery system is purged of air in the delivery line. This purging is achieved before insertion of the over-the-needle catheter in a blood vessel of the patient. The side arm 42 is connected to tubing 14, thence to a socket 76 connected to end 18.

EMBODIMENT OF FIGS. 6 A AND 6 B

Referring next to the over-the-needle catheter and its use, this embodiment is very similar to the over-the-needle catheter of FIG. 5, but the I.V. tubing 14 connected to the side arm 42 is depicted with an additional bacteria exclusion filter 78. This filter is interposed between hub 38, a connector 18 (FIG. 1 A) or the bottle 10. In FIG. 6 A, the purged catheter 26 and needle 24 are inserted into the patient 34 and into the vessel 32. The fluid flow passes through filter 78 when the clamp releases the flow. In FIG. 6 B, the disposed catheter arrangement is repeated, but the needle 24 and connected needle holder with flash-back indicator 30 are shown as removed from the slit valve of FIG. 3.

EMBODIMENT OF FIG. 7

Referring to FIG. 7, wherein like reference characters indicate like parts as above, the sealing valve may also utilize a resilient disc 80 without a preformed slit for the passage of the needle 24 (not shown). Threaded cap 44 (not seen in this view) is utilized to compress this disc 80 between like washers 50 which are the same or similar to those shown and described in conjunction with FIG. 3.

EMBODIMENT OF FIGS. 8 A AND 8 B

Referring next to the fragmentary views which diagrammatically show an alternate means for providing a passageway for the flow of air and drops of fluid. Although the slit or puncture 40 of the catheter is a preferred procedure, it is of course realized that the tight forward end of the catheter and the needle shank could be formed to provide a very small passageway thereby. The needle 24 may be made with locally formed groove or dimple 82 sufficient for the passing of air and fluid under a small amount of pressure. Instead of local alterations to the shank of the needle 24, the tip of the catheter bore may be formed so that at least locally a small passageway may be provided. Alteration of the sliding bore of the catheter tip may be by many means and, except for the novelty of providing such an air and fluid passageway in conjunction with the needle, may utilize known devices.

FIG. 8 A shows in a greatly enlarged scale a fragmentary sectional view showing the needle 24 with a small dimple 82 which may be produced by a hammer device but may also be formed by an abroding action. FIG. 8 B is a very fragmentary diagrammatic view taken on the line 8 B–8 B and showing the dimpled portion 82 of the needle 24. Not shown is an alteration of the catheter tip which may be produced by heated or mechanical means and is only intended to locally provide a less than a tight slide fit of the catheter and needle shank.

EMBODIMENTS OF FIGS. 9 A, 9 B, 9 C AND 9 D

Referring next and finally to the showing of FIGS. 9 A, 9 B, 9 C and 9 D there is disclosed a bayonet-type retainer for use with the resilient disc and washers as a means of exerting a determined compressive force on the resilient disc just prior to the time of use. The disc utilized may be with a slit as shown in FIG. 3 or may be an unslit disc as seen in FIG. 7. An important and novel actuation as provided by this embodiment is to provide just prior to the time of use an established compressive force on the resilient disc. This compressive force provides the required and desired sealing of the hole in the disc when and as the needle 24 is withdrawn by the practitioner. This alternate means provides a positive and pre-selected force actuation of and on the compressing of the resilient disc.

In FIG. 9 A the showing, mostly in section; is very much like the showing of FIG. 4 with needle 24 secured in holder-indicator 30. Catheter 26 is secured in the forward end of a catheter hub now identified as 100 and having a side arm 102 much like side arm 42 in FIG. 3 and 4. This hub 100 is formed with a smooth exterior sized and configured to provide a sliding fit with a cap 104 having at least one bayonet groove 106. In FIG. 9 A this groove mates with and is slideably engaged by and with a pin 108 secured to and extending from the catheter hub 100. This cap 104 has an inner tubular portion 110 having a forward end adapted to engage the rear end of a compression spring 112. The forward end of this spring 112 is adapted to engage the face of a washer 50. The seal of the rear end of the catheter hub 100 may employ either the disc and washers of FIG. 3 or the disc and washers of FIG. 7. In the FIG. of 9 A the spring 112 is in the expanded condition with a minimum of compressive force on a retained resilient disc identified as 114.

In FIG. 9 B is shown the forward pushing of cap 104 so that the pin 108 is caused to reach the end of the groove 106 and with a small rotation is caused to be retained in the hook end identified as 116. This pin 108 and groove 106 establish the limit of forward movement and rotation provides the lock of pin 108 in the hook end 116. The compressive force of and in the spring 112 establishes the force on the disc 114. This force amount is a matter of selection and design but it is contemplated that the attendant by this means provides a predetermined exerting force on the resilient disc 114 when and as the cap 104 is moved into the locked position of FIG. 9 B.

In FIG. 9 C the exterior view of this bayonet-lock concept is diagrammatically depicted. Cap 104 is shown with one groove 106 and one pin 108 but this is a matter of selection. It is contemplated that two or three pins and grooves may be provided in the device as and when desired.

In FIG. 9 D there is shown a tubular member identified as 120. This tubular member is of resilient material and has an aperture 122 therethrough for the through passage of the needle 24. This resilient tubular member 120 is illustrated to note that a compressive force other than a spring may be used with the bayonet-type lock apparatus of FIG. 9 C. Instead of spring 112, this member 120 is compressed with the forward movement of cap 104. This resilient member 120 may be of rubber or the equivalent as long as the desired force is developed when and as this member is compressed by and with the forward actuation.

USE AND OPERATION

The "closed system" over-the-needle I.V. catheter and the several assembled components of FIG. 2 contemplate using a bottle 10, wire bail 11, spike 75, drip chamber 12, I.V. tubing 14, flow-control device such as a roll clamp 16 or pump (not shown), and probably a connector 18. In the arrangement of FIGS. 6 A and 6 B, the tubing 14 is shown attached directly to the side arm 42 while the arrangement of FIG. 5 contemplates connector 18 mounted in socket 76. The filter 78 in said delivery line is seen in FIGS. 6 A and 6 B. In both arrangements the cap 44 is initially tightened to place a compressive stress on the disc 54 after which fluid is fed to the catheter 26 and purging of air in the line is confirmed by the release of a few drops of fluid 22 through the opening 40 in the catheter. When purging the line of air, the catheter assembly is held such that the catheter tip is up. In this manner, all air is expelled from the system. As noted above, this fluid is delivered through conductor 14 into the cavity 66 (FIG. 4) and flows through passageway 64 to said slit or puncture 40. The filter 78 (FIGS. 6 A and 6 B) is contemplated to exclude bacteria from delivery to the side arm. This filter is usually of a pore size of 0.22 microns. With or without a filter, the purging of air and filter with fluid may be provided by an arrangement such as that shown in FIGS. 8 A and 8 B as described above.

The resilient disc may or may not have a slit as above noted and described. The venipuncture procedure is now performed in the usual manner. After venipuncture is achieved, the needle holder assembly 30 is removed by pushing off the catheter assembly 26 and insuring the catheter is inserted in the patient's blood vessel 32. As the shank of the needle 24 exits from the catheter hub 38 or 100, the pre-compressed resilient seal closes, preventing any blood or other fluid from exiting the catheter hub. In a normal manner the catheter 26, catheter hub (38 or 100) and the attached and connected tubing 14 is taped to the patient's arm, hand, etc. Whether with a rotative action for threaded cap 44 of FIG. 3 or the bayonet-type cap 104 of FIG. 9 C, it is contemplated that the resilient disc is compressed just prior to insertion. Examples of tests which have been conducted on the above construction resulted in the following:

EXAMPLE I

An over-the-needle I.V. catheter needle seal was assembled using two acrylic washers one-quater inch in diameter with an inside diameter of 0.052 inches. Pieces of Silicone cord of one-quarter inch in diameter were cut to a thickness of 0.045 inches, with the silicone cord (disc) having a durometer of Shore A-50. The units were assembled by placing first one acrylic washer into the catheter hub, followed by the cut silicone cord which was followed by the other acrylic washer. The cap 44 was threaded half way up the catheter hub. This allowed the washers and disc to be in a stress-free environment. Next, the introducer needle 24 was inserted through the hub and through the washers, also piercing the silicone disc. An administration set was attached to the sideport 42 of the catheter hub unit with a female luer on the end. The units were sealed in Tyvek pouches and sterilized. ETO exposure was 600 mg/liter of gas per cycle.

After sterilization, the units were aged and then tested for fluid leakage and to determine the fluid pressure that the seals could hold.

The unit packages were opened and the catheter hub cap 44 tightened until finger-tight. Each catheter 26 was inserted into a closed hollow tube to seal off the tip of the catheter as well as the introducer needle 24 without sealing them off from each other. The line set pressure was from an attached thirty-six inches of tubing providing a fluid head and each unit was primed with water until drops of water were seen coming out of the slit 40 in the catheter 26. The introducer needle 24 was then removed and the seals examined for leakage. There were no leaks.

Next, each line set was clamped off and a syringe with pressure gauge was attached to the catheter end of the assembly. A test pressure of 30 psi was applied to each unit with no leakage.

EXAMPLE II

See Example I except for the following:

Latex discs one-quarter inch in diameter by 0.062 inches thick were used. Durometer was Shore A-40. Results obtained were the same as Example I.

Gum Rubber was another material that was evaluated. Thicknesses of sealing discs varied from 0.045 inches through 0.125 inches with comparable results.

When one-eighth inch thick sealing discs were used with silicone rubber having a Shore A-70 durometer, the drag force on the needle became appreciable and made it difficult for the needle to be removed.

In either embodiment, the "closed system" providing an over-the-needle I.V. catheter anticipates that after confirmation of purging of air, the needle and catheter are inserted into the patient's blood vessel. After the desired placement has been determined by the flashback of blood to and into the indicator 30, the needle 24 is withdrawn. Prior to needle placement, the threaded cap 44 is rotated so that the disc 54 is compressed and opening 56 created either by a slit or due to needle puncture is caused to close against the flow of blood when needle 24 is withdrawn. Whether the threads provided on the hub molding 38 are of an ACME style or another, it is contemplated that the threads 60 in and of the cap 44 mate with those of and in the hub 38 so that a small rotational manipulation causes the disc 54 to be sufficiently compressed to effect a slit-closing of the passage to eliminate fluid flow.

As conventionally provided, the catheter 26 is of flexible plastic, generally Teflon (TM DuPont), and the opening 40 is into the larger diameter portion 64 adjacent to and rearwardly of the tapered forward portion 62. The elastomeric valve includes washers 50 (preferably two) and the disc 54, which is conventionally of rubber or like resilient material. The slit 56 is made sufficient for the passage therethrough of the shank of needle 24 but, when compressed between the washers 50, is sufficient to effect a stop valve to the flow of fluid when and as the needle is withdrawn.

In two embodiments of this invention, the catheter is shown with a small slit 40, which may also be a small puncture as would be made by the sharpened end of a needle. This puncture is sufficient to pass air and also fluid under a small amount of pressure, but when the needle 24 is withdrawn from the catheter 26 this slit or puncture is essentially sealed or closed so that blood from the patient does not flow through this slit or puncture. The slit or puncture is ideally very close to the tapered front end of the catheter and is defined as means for venting air within the connected system. The purging of air is confirmed when and as a small drop of fluid is expelled through said catheter 26.

The catheter 26 may be secured by molding in place, by adhesive or may be by mechanical means such as a ferrule which may include guiding means for the sharpened end of the needle 24 as it is inserted to and through the catheter. The forward end of the catheter is conventionally formed with a tapered end which is a tight fit to the needle so as to assist in the placement and penetration. The slit valve closure of the rear end of the catheter hub is an inexpensive means for achieving a seal of the passage after withdrawal of the needle. Absent manipulation at the time just prior to use and withdrawal of the needle, a "set" of the resilient member usually occurs because of storage time, sterilization procedures, or both.

The alternate showings in FIGS. 8 A, 8 B, 9 A, 9 B, 9 C and 9 D are illustrative of how this over-the-needle catheter and introducer needle apparatus may be constructed and used. The present preferred means for providing an air escape at the tip end of the catheter 26 is by the slit or puncture 40. Whether a threaded cap 44 or a bayonet-lock device as in FIGS. 9 A through 9 D is used is a matter of preference. The resilient disc is compressed to effect a seal of the withdrawn needle 24. This force of compression of the resilient disc is with actuation at the time of use and just prior to insertion.

Positioning of a small passage for air and the like is defined as "at or near the proximal end of the flexible catheter." Positioning of this small passage may be selected by the constructor of the catheter device, but it is important that any variation in positioning be such that this small passage is interior of the skin of the patient, and preferably within the pierced blood vessel, so that with the catheter placed and in use this passage is not open to atmosphere.

What is claimed is:

1. A closed system over-the-needle I.V. catheter product which is attached to an I.V. fluid delivery means and primed prior to puncture of a blood vessel and retention of said catheter in a patient, said I.V. catheter product including:
   a catheter hub having an opening adapted to received fluid from an I.V. fluid supply, this opening being flow-connected to a longitudinal passage formed therein and with this catheter hub having a front end flow-connected to this passage an with this catheter hub having an open rear end;
   a bacteria-retentive filter serially connected to said I.V. fluid delivery means, with said retained filter adapted to pass I.V. fluid and to exclude any bacteria present in said delivered fluid supply to said catheter hub;
   a needle with holder attached thereto so that when and as the needle makes a puncture of a blood vessel in a patient, blood flows through the needle to the holder;
   a flexible catheter positioned at the front end of the catheter hub and flow-connected to said longitudinal passage, said catheter having an entering end with a contour providing a tight fit to and on said needle, this catheter sized to provide a small conducting passageway alongside the placed needle;
   a small passage means provided at or near the distal end of the flexible catheter, this small flow-passage means providing for the expelling of air from a localized area at or in this contoured entering end, this expulsion occurring as fluid is advanced through the system; and
   means arrayed at the open rear end of the catheter hub for closing this rear end and sealing off the needle passage as and when the needle is removed from the catheter and catheter hub said means includes forming said open rear end with an exterior male thread and with a shouldered recess in said end and utilizing a compressible, pierced resilient disc to close the passageway by the withdrawal of the needle and a washer arrayed on each side of the resilient disc and with the resilient disc further compressed as desired by rotative manipulation of a threaded cap having female threads configured to mate with the male threads formed on the catheter hub, said cap manipulated to 2. A "closed system" catheter product as in claim 1 in which the forming of the entering end of the catheter is a taper which brings the distal end of the catheter to a very thin edge which is contiguous with the needle.

3. A "closed system" catheter product as in claim 2 in which the flexible catheter, except at the contoured end, is a tube whose inner diameter is at least one-thousandth of an inch greater than the outer diameter of the needle.

4. A "closed system" catheter product as in claim 1 which further includes providing with the needle holder and in flow communication with the needle, an indicator device showing blood flow when and as the patient's blood vessel is penetrated.

5. A "closed system" catheter product as in claim 1 in which the small flow-passage means provided in the tip end of the catheter is made as a very small slit and produced by a very sharp and thin member such as a razor blade.

6. A "closed system" catheter product as in claim 1 in which the small flow-passage means provided in the tip end of the catheter is made as a very small puncture as by a sharpened end of a small needle and the like.

7. An over-the-needle catheter comprising
   a hub;
   a hollow catheter extending from said hub;
   a sealing disc within said hub, said disc having a thickness less than a cross-sectional dimension thereof and in a range of from 0.045 inches to 0.125 inches;
   a hollow needle extending through said catheter and through said disc in sealed relation;
   a needle holder connected to said needle and having a flashback chamber in communication with said needle for receiving an indication of blood therein; and
   means for selectively compressing said disc longitudinally to impose a compressive force on said disc sufficient to seal said disc against said needle during venipuncture and to close any opening therein after withdrawal of said needle from said disc, said means being movable between an initial release position with said disc in an uncompressed state and a clamping position to impose said compressive force on said disc.

8. A catheter as set force in claim 7 wherein said means includes a member mounted on said hub for movement between said release position and said clamping position relative to said hub to impose said compressive force on said disc in said clamping position.

9. A catheter as set force in claim 8 wherein said member is threadably mounted on said hub for relative rotation between said positions.

10. A catheter as set force in claim 8 wherein said member is slidably mounted on said hub for longitudinal movement between said positions.

11. A catheter as set force in claim 7 wherein said disc has a preformed slit for penetration of said needle therethrough. said compressive force on said rings to compress said disc therebetween in said clamping position.

12. A catheter as set force in claim 7 wherein said means includes a coil spring coaxially abutting said disc and a member mounted on said hub for movement between a release position and a clamping position relative to said hub to impose said compressive force on said spring to compress said disc in said clamping position.

13. A catheter as set force in claim 7 which further comprises a hollow side arm extending laterally from said hub in sealed relation to communicate with said catheter and adapted to be connected to an administration set.

14. A catheter as set force in claim 7 wherein said disc is made of resilient material.

15. A catheter as set force in claim 7 wherein said means includes a compressible tubular member abutting said disc and a member mounted on said hub for movement between said release position and said clamping position relative to said hub to impose said compressive force on said tubular member to compress said disc in said clamping position.

16. A catheter as set force in claim 7 wherein said catheter has a tapered distal end contiguous with said needle.

17. A catheter as set force in claim 16 wherein said catheter has an inner diameter at least one-thousandth of an inch greater than an outer diameter of said needle.

18. An over-the-needle catheter comprising
    a hub;

a hollow catheter extending from said hub;
a sealing disc within said hub;
a hollow needle extending through said catheter and through said disc in sealed relation;
a needle holder connected to said needle and having a flashback chamber in communication with said needle for receiving an indication of blood therein; and
means for selectively compressing said disc longitudinally to impose a compressive force on said disc sufficient to seal said disc against said needle during venipuncture and to close any opening therein after withdrawal of said needle from said disc, said means including a pair of rings having said disc therebetween and a member mounted on said hub for movement between a release position and a clamping position relative to said hub to impose said compressive force on said rings to compress said disc therebetween in said clamping position.

19. An over-the-needle catheter comprising
a hub;
a hollow catheter extending from said hub;
a sealing disc within said hub;
a hollow needle extending through said catheter and through said disc in sealed relation, said catheter and said needle being disposed in sealed relation to each other at distal ends thereof;
a needle holder connected to said needle and having a flashback chamber in communication with said needle for receiving an indication of blood therein;
means at said distal end of one of said catheter and said needle for venting air from between said catheter and said needle; and
means for selectively compressing said disc longitudinally to impose a compressive force on said disc sufficient to seal said disc against said needle during venipuncture and to close any opening therein after withdrawal of said needle from said disc.

* * * * *

UNITED STATES PATENT AND TRADEMARK OFFICE
CERTIFICATE OF CORRECTION

PATENT NO. : 4,966,586

DATED : October 30, 1990

INVENTOR(S) : VINCENT L. VAILLANCOURT

It is certified that error appears in the above-identified patent and that said Letters Patent is hereby corrected as shown below:

```
Column 2, line 48 change "produce" to -product-
Column 3, line 38 change "with filter" to -with the filter-
Column 8, line 38 change "catherter" to -catheter-
Column 9, line 25 change "abroding" to -abrading-
Column 13, line 6 change "received" to -receive-
Column 13, line 10 change "an" to -and-
Column 13, line 47 after "manipulated to" insert -provide the
      desired needle-sealing capability of the resilient disc.-
Column 14, lines 39 to 40 cancel "said compressive ... clamping
      position"
```

Signed and Sealed this

Fourth Day of August, 1992

Attest:

DOUGLAS B. COMER

Attesting Officer

Acting Commissioner of Patents and Trademarks